United States Patent [19]

Segall et al.

[11] Patent Number: 4,990,708

[45] Date of Patent: Feb. 5, 1991

[54] PROCESS FOR THE PREPARATION OF DIBROMOMETHANE

[75] Inventors: Jeane Segall; Leonard M. Shorr; Michel Adda, both of Haifa, Israel

[73] Assignee: Bromine Compounds Limited, Beer-Sheva, Israel

[21] Appl. No.: 350,398

[22] Filed: May 11, 1989

[30] Foreign Application Priority Data

May 12, 1988 [IL] Israel .......................................... 86357

[51] Int. Cl.$^5$ ............................................... C07C 17/10
[52] U.S. Cl. .................................... 570/253; 570/252; 570/254; 570/255
[58] Field of Search ............... 570/241, 252, 255, 253, 570/254, 258

[56] References Cited

U.S. PATENT DOCUMENTS

| | | | |
|---|---|---|---|
| 1,939,292 | 12/1933 | Carlisle | 570/255 |
| 1,964,868 | 7/1934 | Berndt et al. | 570/255 |
| 2,244,629 | 6/1941 | Iwak et al. | 570/258 |
| 2,406,195 | 8/1946 | Cass | 570/258 |
| 3,848,007 | 11/1974 | Forlano | 570/255 |
| 3,983,180 | 9/1976 | Habata et al. | 570/258 |

FOREIGN PATENT DOCUMENTS

| | | | |
|---|---|---|---|
| 565122 | 11/1932 | Fed. Rep. of Germany | 570/253 |
| 1392045 | 2/1965 | France | 570/255 |

*Primary Examiner*—Howard T. Mars
*Attorney, Agent, or Firm*—Michael N. Meller

[57] ABSTRACT

A process for the preparation of dibromomethane is described, in which gaseous methyl bromide and bromide are reacted as temperatures of 300° C. or higher. The reaction is highly selective to DBM and almost quantitative $Br_2$ conversion is obtained in the absence of catalysts.

8 Claims, 1 Drawing Sheet

PROCESS FOR THE PREPARATION OF DIBROMOMETHANE

FIELD OF THE INVENTION

The present invention relates to a process for the manufacture of dibromomethane. More particularly, the invention relates to a process by means of which dibromomethane is produced by the thermal bromination of methyl bromide.

BACKGROUND OF THE INVENTION

Dibromomethane (DBM) is an important solvent and chemical intermediate which is used in a large number of industrial applications. DBM is normally produced by the catalyzed halogen exchange of bromine for the chlorine contained in dichloromethane (DCM). One such process is described in German Patent No. 727,690. This process suffers from a number of drawbacks. The source of bromine is dry, gaseous HBr, which often contains considerable amounts of hydrogen, deriving from its manufacturing process. Hydrogen, being an inert gas in the DBM process, flows through the reactor, sweeping out part of the volatile DCM before it has time to react, thus decreasing the efficiency of the conversion. In addition, DCM is an expensive raw material, considering that 83% of its weight is wasted as HCl along with the excess HBr which is employed, making for an ecological problem. Disposal of spent catalyst is an additional ecological problem.

Other processes known in the art employ bromine salts instead of HBr. These processes, however, are inefficient and are not used in actual industrial applications. Thus, for example, $NH_4Br$ in dimethylformamide (Neth. Appli. No. 6,607,498), and NaBr (U.S. Pat. No. 3,923,914) have been used for such purposes.

Direct bromination of methane at high temperatures has also been attempted, but resulted in low yields and reaction selectivity. Thus, for instance, German Patent No. 330,642 obtained a maximum of 44,4% DBM at 370° C., in the presence of an iron catalyst.

SUMMARY OF THE INVENTION

It has now been found, and this is an object of the present invention, that DBM can be prepared by a non-catalytic, non-photochemical bromination of methyl bromide, with a high selectivity to DBM. Under appropriate conditions, an almost quantitative $Br_2$ conversion is obtained.

The selectivity of the process to DBM can be increased even more by recycling the by-product bromoform (and $CBr_4$, if any) to the reaction zone where it is debrominated to DBM in a reverse reaction. Therefore, essentially the only process by-product is HBr, which is an industrially useful material and which can be utilized, as will be detailed further below. Thus, no ecological problem exists. On the other hand, bromoform can be obtained as a valuable by-product, if desired.

DETAILED DESCRIPTION OF THE INVENTION

Figure 1:
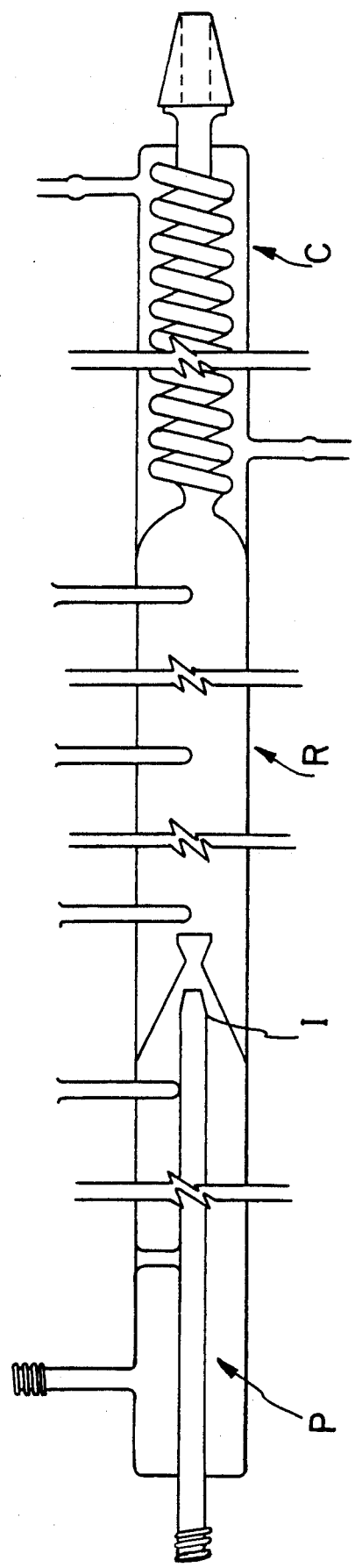

The process of the invention comprises continuously reacting gaseous methyl bromide and bromine at a reaction temperature of at least 300° C., and with a small methyl bromide conversion per pass. The reaction is strongly dependent on the temperature and, therefore, higher temperatures are preferred for obtaining high conversions. On the other hand, decomposition of DBM is known to set in above 400° C., so that the maximal reaction temperature is limited. The preferred temperature range for the process should be within 350° C.–410° C., 400° C. being the most preferred temperature.

A number of acidic and active surface catalysts have been found, which allow for the reduction of the reaction temperature. Thus, for example, with infusorial earth, $FeCl_3$, $ZnCl_2$, active carbon and pumice, reaction takes place at about 100° C. lower than without catalyst. However, operation in an unencumbered free-space reactor is generally found to be more convenient. As will be apparent to the skilled person, different catalysts can be employed in the process of the invention. The use of a catalyst, however, does not substantially alter the process of the invention and can exploit the advantages provided by the invention.

The initial molar ratio of methyl bromide:bromine is also an important parameter, and the selectivity of the reaction depends on the dilution of bromine in the reaction mixture. Thus, at a 1:1 ratio, a typical product distribution is: 42% mole $CH_2Br_2$; 49% $CHBr_3$ and 9% $CBr_4$. At a molar ratio of 50:1, on the other hand, 96% of the product is $CH_2Br_2$, the remaining 4 mole % being $CHBr_3$.

It is therefore clear that, in order to obtain high selectivity, it is necessary to work at high initial molar ratios, with consequent low conversions of methyl bromide per pass, and high methyl bromide recycle ratios. When a $CH_3Br:Br_2$ molar excess of about 10:1 is employed, a 80% molar selectivity to $CH_2Br_2$ is obtained. The selectivity increases to 95–96% molar, when 50:1 molar excesses are used. Unreacted $CH_3Br$ is recycled to the reactor after condensing out the higher bromomethanes. DBM (b.p. 98° C.) is easily obtained in a pure state, free of bromoform (b.p. 151° C.), by distillation.

The above and other characteristics and advantages of the process of the invention will be better understood through the following illustrative and non-limitative description of experiments and experimental results.

EXPERIMENTAL SYSTEM

The reaction system comprises a vertically mounted glass column, either empty or filled with Wilson glass helices (d=0.03 cm) and electrically heated by a coil made from heating tape (Electrothermal HC 103). Bromine is fed into the column through a Sage syringe pump, and methyl bromide (kept in a 500 ml Fisher pressure bottle) is fed through a calibrated flow meter. The loss in weight of the methyl bromide container is measured periodically. The products leaving the heating zone are cooled and the liquid products collected in a water cooled receiver, the condensable gaseous products in an ice-cooled trap, and the exit HBr in water. A preheater, kept at 230°–290° C., was used in a few experiments.

EXAMPLE 1

The glass reactor (L=23 cm, D=2.6 cm) filled with Wilson glass helices (d=0.03 cm) was heated to 390° C. The temperature was measured by means of a thermocouple inserted into the middle of the column. Bromine, 63.8 g (0.4 mole), was placed in a 25 ml syringe in the Sage pump, and the addition adjusted to 0.25 gr/min. Gaseous methyl bromide was fed into the heated column, through the flow meter, at a rate of 0.80 g/min. A total of 200 g (2.1 moles) of $CH_3Br$ was fed during 251 minutes. The addition of both reagents was constant throughout the reaction. The gases leaving the column were condensed in a water-cooled receiver, then an ice-cooled trap, and finally absorbed in water.

At the end of the reaction, after cooling the reactor, a slow $N_2$ stream was passed through, in order to flush out any residual products from the column. It was then washed with methylene chloride. The two traps and the methylene chloride washing were united, washed with water to remove the HBr, cooled in ice and reacted with a 40% solution of $NaHSO_3$ to remove traces of residual $Br_2$, if present. After separation, the organic phase was dried over anhydrous $Na_2SO_4$. 113.2 g of product were obtained, with 91.9% $Br_2$ conversion. Product analysis. $CH_3Br$: 18.8%; $CH_2Cl_2$ (solvent): 38.3%; $CH_2Br_2$: 29.5%; $CHBr_3$: 13.3%; $CBr_4$: 0.29%.

EXAMPLE 2

Several experiments were carried out in a manner similar to Example 1, varying the operating parameters. The results of these experimental runs are set forth in Table I below.

EXAMPLE 3

Example 1 was repeated, but employing a glass column without packing (Wilson helices). The results are detailed in Table II below.

EXAMPLE 4

Liquid $CH_3Br$ exits a holding tank (10 liters) and vaporizes in a heat exchanger. The flow is controlled by a micrometric valve and is measured by a thermal mass flowmeter (Porter) and/or a rotameter (Gilmont). The $CH_3Br$ is mixed with recycle bromoform and $CBr_4$, if any, and fed to a glass reactor. Bromine is pumped from a 1 liter bottle with a peristaltic pump (Watson-Marlow). The flowrate is controlled by the pump and measured by means of a balance.

A scheme of the reactor is given in FIG. 1. It is made of three sections:

Section 1: Preheater (P) - $CH_3Br$ is heated therein to a temperature 20° to 30° C. below the reaction temperature. Bromine vaporizes in the internal tube.

Section 2: Reactor (R) - $CH_3Br$ (or the mixture $CH_3Br$/bromoform) and bromine are mixed by means of an injector at the entrance to the reaction zone. The volume of the reaction zone is 500 ml. The temperature is controlled at the center of the reactor.

Section 3: Cooler (C) - The gases are cooled with air. The temperature at the bottom of the cooler is between 100° and 150° C.

Before operation, the system is evacuated to eliminate any traces of air. A purge system, constituted of a peristaltic pump (Watson-Marlow), withdraws 5-10% of the circulating stream. The $CH_3Br$ condenses in an acetone/Dry Ice trap and any air present exits to the atmosphere. The liquid $CH_3Br$ returns to the recirculating stream through a siphon.

$CH_3Br$ is preheated in the preheater P and then mixed with $Br_2$ in the injector I. The reaction takes place in the reactor R. After cooling, the liquid fraction which contains organic products, residual $Br_2$ and dissolved $CH_3Br$, are separated from the gas fraction in a mist separator. Most of the $CH_3Br$ dissolved in the product is separated in a separation column. In the reservoir is obtained a product which contains residual $Br_2$ and 5-10% $CH_3Br$. The gaseous fraction which contains $CH_3Br$, HBr and traces of $Br_2$ and DBM passes through an absorption column and is washed free of HBr and $Br_2$ with water. It is then pumped by a diaphragm pump and dried in a $CaCl_2$ column. After adding $CH_3Br$ make-up (and bromoform, if desired) it is recirculated to the reactor. DBM is isolated from the liquid fraction by distillation.

A series of experiments was carried out, according to the above-detailed procedure and under varying conditions. The results obtained are summarized in Table III.

EXAMPLE 5

Example 4 was repeated at 410° C., and with a 6.5 seconds residence time, using a feed which was made up to contain, in addition to $CH_3Br$ and $Br_2$, also bromoform recovered by distillation from a previous run. The molar ration of $CH_3Br$:$Br_2$:bromoform in the feed was 10:1:0.1. At a $Br_2$ conversion of ~99%, the product distribution (on a $CH_3Br$ free basis) was (in mole percent): 90% DBM, 9% bromoform and 1% $CBr_4$. Thus in this experiment, by recycling the bromoform, essentially only DBM was produced.

The crude product was treated with aqueous sodium bisulphite to remove the residual $Br_2$, washed with water to neutral pH and distilled under an inert atmosphere ($N_2$) and eventually under reduced pressure, through an Oldershaw plate column (L=50 com, D=2 cm). DBM, >99.5% pure and bromoform 98% pure were obtained.

EXAMPLE 6

A number of bromination reactions were carried out using different catalysts. When about 0.1 moles of $CH_3Br$ were reacted with about 0.1 moles of $Br_2$, employing pumice as the support, and 10% $FeCl_3$; 10% $ZnCl_2$ as the catalyst, 30% of bromination was obtained at a reaction temperature of 250°-270° C., 88% bromination at 300°-320° C. and 97% bromination at 350°-360° C. As a comparison, the reaction was carried out with glass tubing (5 mm OD glass tubing, cut to length of about 8 mm), and only 67% of bromination was obtained at 300°-320° C. reaction temperature. Similar temperature reduction can be observed using active carbon.

The above description and examples have been given for the purpose of illustration and are not intended to be limitative. Many variations can be effected in the various operating conditions, without exceeding the scope of the invention.

TABLE I

| | | | | | Bromination of Methyl Bromide | | |
| | | | | | Product Distribution[b] | | |
| Temp °C. | Run Time (Hours) | $CH_3Br/Br_2$ Ratio | Total Feed Rate (g/hour) | Residence Time (sec) | $CH_2Br_2$ mole % | $CHBr_3$ mole % | $CBr_4$ mole % |
| --- | --- | --- | --- | --- | --- | --- | --- |
| 300 | 1.2 | 1/1 | 22 | 26 | 53 | 45 | 2 |
| 350 | 2 | 1/1 | 13 | 40 | 42 | 49 | 9 |

TABLE I-continued

Bromination of Methyl Bromide

| Temp °C. | Run Time (Hours) | CH$_3$Br/Br$_2$ Ratio | Total Feed Rate (g/hour) | Residence Time (sec) | Product Distribution[b] CH$_2$Br$_2$ mole % | CHBr$_3$ mole % | CBr$_4$ mole % |
|---|---|---|---|---|---|---|---|
| 350 | 2 | 2/1 | 18 | 27 | 60 | 35 | 5 |
| 350 | 2 | 4/1 | 27 | 16 | 75 | 23 | 2 |
| 370[a] | 2 | 5/1 | 29 | 45 | 73 | 27 | 0.3 |
| 390 | 4.2 | 5.3/1 | 63 | 9 | 76 | 24 | 0.4 |
| 390 | 1.5 | 7.2/1 | 87 | 2 | 79 | 21 | 0.2 |
| 390 | 2 | 14.8/1 | 31 | 6 | 83 | 16 | 0.9 |
| 390 | 1.6 | 24.7/1 | 50 | 4 | 92 | 7 | 0.2 |
| 390 | 1.7 | 50/1 | 75 | 2 | 96 | 4 | 0 |

[a]Preheated. Preheater consisting of column (L = 29 cm, D = 2.6 cm) kept at 230° C.. Residence time calculation includes the preheater zone
[b]On methyl bromide free basis.

TABLE II

Bromination in Glass Column Without Packing

| Temp °C. | Run Time (Hours) | CH$_3$Br/Br Ratio | Total Feed Rate (g/hour) | Residence Time (sec) | CH$_2$Br$_2$ mole % | CHBr$_3$ mole % | CBr$_4$ mole % |
|---|---|---|---|---|---|---|---|
| 390 | 2.7 | 5.2/1 | 70 | 12 | 65 | 33 | 2 |
| 390 | 1.8 | 4.3/1 | 47 | 18 | 71 | 28 | 1 |
| 390[c] | 0.93 | 4.6/1 | 64 | 9 | 76 | 24 | 0.4 |

[b]On methyl bromide free basis.
[c]Packed column.

TABLE III

| Temp °C. | CH$_3$Br/Br Ratio | Bromine Conversion % | Residence Time (sec) | Product Distribution[a] CH$_2$Br$_2$ mole % | CHBr$_3$ mole % | CBr$_4$ mole % |
|---|---|---|---|---|---|---|
| 390 | 20:1 | 97.5 | 4 | 91.1 | 8.8 | 0.1 |
| 390 | 20:1 | 93.2 | 2.5 | 88.7 | 11.0 | 0.3 |
| 390 | 10:1 | 94.3 | 4 | 85.5 | 13.9 | 0.6 |
| 390 | 10:1 | 98.7 | 6.5 | 83.6 | 16.3 | 0.1 |
| 390 | 5:1 | 86.0 | 4 | 72.5 | 25.3 | 2.1 |
| 390 | 20:1 | 99.3 | 6.5 | 88.5 | 11.5 | 0.1 |
| 390 | 20:1 | 95.7 | 2.5 | 83.5 | 15.9 | 0.6 |
| 390 | 10:1 | 88.0 | 2.5 | 83.2 | 15.9 | 0.9 |
| 390 | 10:1 | 91.8 | 4 | 84.5 | 14.8 | 0.7 |
| 400 | 10:1 | 97.4 | 4 | 76.3 | 23.2 | 0.5 |
| 400 | 10:1 | 95.3 | 2.5 | 82.0 | 17.4 | 0.5 |
| 410 | 10:1 | 94.0 | 2.5 | 80.4 | 19.0 | 0.6 |
| 410 | 10:1 | 98.0 | 2.5 | 77.6 | 21.9 | 0.5 |
| 410 | 10:1 | 99.0 | 6.5 | 80.4 | 19.4 | 0.2 |
| 400 | 10:1 | 97.2 | 6.5 | 74.6 | 24.9 | 0.5 |
| 380 | 10:1 | 91.6 | 6.5 | 80.6 | 18.1 | 1.3 |
| 370 | 10:1 | 85.8 | 6.5 | 78.9 | 19.6 | 1.5 |
| 360 | 10:1 | 82.2 | 6.5 | 82.1 | 16.3 | 1.6 |

[a]On methyl bromide free basis.

We claim:

1. A process for the preparation of dibromomethane, in which gaseous methyl bromide is reacted with bromine at a reaction temperature of at least 300° C., and a molar ratio of CH$_3$Br:Br$_2$ of at least 10:1.

2. A process according to claim 1, wherein the reaction temperature is about 400° C.

3. A process according to claim 1, wherein the molar ratio of CH$_3$Br:Br$_2$ is about 50:1.

4. A process according to claim 1, wherein by-products are removed from the product stream of dibromomethane by distillation.

5. A process according to claim 4, wherein the by-products comprise CHBr$_3$ and/or CBr$_4$.

6. A process according to claim 4, wherein the by-products are recycled to the reaction zone.

7. A process according to claim 1, wherein the reaction is carried out in the presence of a catalyst.

8. A process according to claim 5, wherein the by-products are recycled to the reaction zone.

* * * * *

UNITED STATES PATENT AND TRADEMARK OFFICE
CERTIFICATE OF CORRECTION

PATENT NO. : 4,990,708

DATED : February 5, 1991

INVENTOR(S) : SEGALL et al.

It is certified that error appears in the above-identified patent and that said Letters Patent is hereby corrected as shown below:

Left Column, title page, item [75], delete "all".

Right Column, title page, in the Abstract, line 3, amend "mide" to read --mine--

Column 1, line 41, amend "44,4%" to read --44.4%--

Column 4, line 28, amend "ration" to read --ratio-- line 51, insert --a-- after "to"

Column 4, Table I, amend headings of last 3 columns to read respectively --$CH_2Br_2$  $CHBr_3$  $CBr_4$-- mole %   mole %   mole %

UNITED STATES PATENT AND TRADEMARK OFFICE
CERTIFICATE OF CORRECTION

PATENT NO. : 4,990,708

DATED : February 5, 1991

INVENTOR(S) : Segall, et al

It is certified that error appears in the above-identified patent and that said Letters Patent is hereby corrected as shown below:

Column 5, Table I, Table II, and Table III,
amend headings of last 3 columns to read, respectively
-- $CH_2Br_2$ $CHBr_3$ $CBr_4$ --
mole % mole % mole %

Signed and Sealed this

Twenty-ninth Day of December, 1992

Attest:

DOUGLAS B. COMER

*Attesting Officer*    Acting Commissioner of Patents and Trademarks

UNITED STATES PATENT AND TRADEMARK OFFICE
CERTIFICATE OF CORRECTION

PATENT NO.   : 4,990,708

DATED        : February 5, 1991

INVENTOR(S)  : SEGALL et al.

Page 1 of 2

It is certified that error appears in the above-identified patent and that said Letters Patent is hereby corrected as shown below:

Left Column, title page, item [75], delete "both" and insert --all--.

Right Column, title page, in the Abstract, line 3, amend "mide" to read --mine--

Column 1, line 41, amend "44,4%" to read --44.4%--

Column 4, line 28, amend "ration" to read --ratio--
          line 51, insert --a-- after "to"

Column 4, Table I, amend headings of last 3 columns to read respectively --$CH_2Br_2$   $CHBr_3$   $CBr_4$--
                                          mole %    mole %    mole %

UNITED STATES PATENT AND TRADEMARK OFFICE
CERTIFICATE OF CORRECTION

PATENT NO. : 4,990,708

DATED : February 5, 1991

INVENTOR(S) : Segall, et al

It is certified that error appears in the above-identified patent and that said Letters Patent is hereby corrected as shown below:

Column 5, Table I, Table II, and Table III,
amend headings of last 3 columns to read, respectively
--$CH_2Br_2$ $CHBr_3$ $CBr_4$--
mole % mole % mole %

This Certificate supersedes Certificate of Correction issued Dec. 29, 1992.

Signed and Sealed this

Thirteenth Day of April, 1993

Attest:

STEPHEN G. KUNIN

Attesting Officer

Acting Commissioner of Patents and Trademarks